(12) United States Patent
Devens, Jr. et al.

(10) Patent No.: US 7,163,523 B2
(45) Date of Patent: Jan. 16, 2007

(54) BALLOON CATHETER

(75) Inventors: Douglas A. Devens, Jr., St. Paul, MN (US); Edward E. Parsonage, St. Paul, MN (US); Tracee Eidenschink, Wayzata, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 54 days.

(21) Appl. No.: 10/787,777

(22) Filed: Feb. 26, 2004

(65) Prior Publication Data
US 2004/0210211 A1 Oct. 21, 2004

Related U.S. Application Data

(60) Provisional application No. 60/450,255, filed on Feb. 26, 2003.

(51) Int. Cl.
*A61M 29/00* (2006.01)

(52) U.S. Cl. .................. 604/96.01; 604/525

(58) Field of Classification Search ........ 604/523–532, 604/19, 148, 96.01, 97.01, 103.06, 103.09, 604/158, 273; 606/194; 623/1.11; 600/585; 138/140–142
See application file for complete search history.

(56) References Cited

U.S. PATENT DOCUMENTS

| 3,733,309 | A | 5/1973 | Wyeth et al. |
|---|---|---|---|
| 3,745,150 | A | 7/1973 | Corsover |
| 3,769,984 | A | 11/1973 | Muench |
| 3,771,527 | A | 11/1973 | Ruisi |
| 3,799,172 | A | 3/1974 | Szpur |
| 3,807,408 | A | 4/1974 | Summers |
| 3,814,137 | A | 6/1974 | Martinez |
| 3,833,004 | A | 9/1974 | Vazquez et al. |
| 3,837,347 | A | 9/1974 | Tower |
| 3,861,972 | A | 1/1975 | Glover et al. |
| 3,889,685 | A | 6/1975 | Miller, Jr. et al. |
| 3,924,634 | A | 12/1975 | Taylor et al. |
| 3,959,426 | A | 5/1976 | Seefluth |
| 3,962,519 | A | 6/1976 | Rusch et al. |
| 3,996,938 | A | 12/1976 | Clark, III |
| 4,035,534 | A | 7/1977 | Nyberg |
| 4,047,868 | A | 9/1977 | Kudo et al. |
| 4,061,707 | A | 12/1977 | Nohtomi et al. |
| 4,079,850 | A | 3/1978 | Suzuki et al. |
| 4,085,757 | A | 4/1978 | Pevsner |

(Continued)

FOREIGN PATENT DOCUMENTS

CA 2347024 11/1995

(Continued)

OTHER PUBLICATIONS

Flash PTCA Balloon, 2 pages Posted on www.boltonmedical.com prior to filing date of U.S. Appl. No. 10/787,777.

(Continued)

*Primary Examiner*—Nicholas Luchessi
*Assistant Examiner*—Theodore J. Stigell
(74) *Attorney, Agent, or Firm*—Fish & Richardson P.C.

(57) ABSTRACT

A catheter, for example, a balloon catheter has a first and second section and a transition between the sections. The sections and the transition are arranged to enhance catheter deliverability.

21 Claims, 7 Drawing Sheets

U.S. PATENT DOCUMENTS

| | | |
|---|---|---|
| 4,105,022 A | 8/1978 | Antoshkiw et al. |
| 4,140,126 A | 2/1979 | Choudhury |
| 4,141,364 A | 2/1979 | Schultze |
| 4,195,637 A | 4/1980 | Gruntzig et al. |
| 4,198,981 A | 4/1980 | Sinnreich |
| 4,213,461 A | 7/1980 | Pevsner |
| 4,222,384 A | 9/1980 | Birtwell |
| 4,233,022 A | 11/1980 | Brady et al. |
| 4,250,072 A | 2/1981 | Flynn |
| 4,581,390 A | 4/1986 | Flynn |
| 4,597,755 A | 7/1986 | Samson et al. |
| 4,627,436 A | 12/1986 | Leckrone |
| 4,627,844 A | 12/1986 | Schmitt |
| 4,636,346 A | 1/1987 | Gold et al. |
| 4,637,396 A | 1/1987 | Cook |
| 4,748,982 A | 6/1988 | Horzewski et al. |
| 4,776,846 A | 10/1988 | Wells |
| 4,782,834 A | 11/1988 | Maguire et al. |
| 4,842,590 A * | 6/1989 | Tanabe et al. ............... 604/524 |
| 4,917,667 A | 4/1990 | Jackson |
| 4,921,483 A | 5/1990 | Wijay et al. |
| 4,976,690 A | 12/1990 | Solar et al. |
| 5,047,045 A | 9/1991 | Arney et al. |
| 5,094,799 A | 3/1992 | Takashige et al. |
| 5,100,381 A | 3/1992 | Burns |
| 5,100,721 A | 3/1992 | Akao |
| 5,100,992 A | 3/1992 | Cohn et al. |
| 5,102,416 A | 4/1992 | Rock |
| 5,108,415 A | 4/1992 | Pinchuk et al. |
| 5,108,420 A | 4/1992 | Marks |
| 5,114,423 A | 5/1992 | Kasprzyk et al. |
| 5,116,318 A | 5/1992 | Hillstead |
| 5,125,913 A | 6/1992 | Quackenbush |
| 5,137,512 A | 8/1992 | Burns et al. |
| 5,147,302 A | 9/1992 | Euteneuer et al. |
| 5,156,857 A | 10/1992 | Wang et al. |
| 5,160,321 A | 11/1992 | Sahota |
| 5,163,949 A | 11/1992 | Bonutti |
| 5,171,221 A | 12/1992 | Samson |
| 5,176,697 A | 1/1993 | Hasson et al. |
| 5,179,174 A | 1/1993 | Elton |
| 5,183,613 A | 2/1993 | Edwards |
| 5,188,593 A | 2/1993 | Martin |
| 5,195,969 A | 3/1993 | Wang et al. |
| 5,195,970 A | 3/1993 | Gahara |
| 5,195,972 A | 3/1993 | Inoue |
| 5,201,706 A | 4/1993 | Noguchi et al. |
| 5,209,728 A | 5/1993 | Kraus et al. |
| 5,209,729 A | 5/1993 | Hofmann et al. |
| 5,223,205 A | 6/1993 | Jackowski et al. |
| 5,226,880 A | 7/1993 | Martin |
| 5,248,305 A | 9/1993 | Zdrahala |
| 5,250,069 A | 10/1993 | Nobuyoshi et al. |
| 5,254,090 A | 10/1993 | Lombardi et al. |
| 5,254,091 A | 10/1993 | Aliahmad et al. |
| 5,254,107 A | 10/1993 | Soltesz |
| 5,263,962 A | 11/1993 | Johnson et al. |
| 5,270,086 A | 12/1993 | Hamlin |
| 5,272,012 A | 12/1993 | Opolski |
| 5,277,199 A | 1/1994 | DuBois et al. |
| 5,279,560 A | 1/1994 | Morrill et al. |
| 5,279,594 A | 1/1994 | Jackson |
| 5,279,596 A | 1/1994 | Castaneda et al. |
| 5,290,306 A | 3/1994 | Trotta et al. |
| 5,304,171 A | 4/1994 | Gregory et al. |
| 5,304,197 A | 4/1994 | Pinchuk et al. |
| 5,306,246 A | 4/1994 | Sahatjian et al. |
| 5,312,356 A | 5/1994 | Engelson et al. |
| 5,318,041 A | 6/1994 | DuBois et al. |
| 5,318,587 A | 6/1994 | Davey |
| 5,330,428 A | 7/1994 | Wang et al. |
| 5,330,429 A | 7/1994 | Noguchi et al. |
| 5,334,146 A | 8/1994 | Ozasa |
| 5,336,205 A | 8/1994 | Zenzen et al. |
| 5,342,307 A | 8/1994 | Euteneuer et al. |
| 5,344,401 A | 9/1994 | Radisch et al. |
| 5,358,486 A | 10/1994 | Saab |
| 5,358,493 A | 10/1994 | Schweich, Jr. et al. |
| 5,364,357 A | 11/1994 | Aase |
| 5,366,472 A | 11/1994 | Hillstead |
| 5,370,655 A | 12/1994 | Burns |
| 5,372,603 A | 12/1994 | Acker et al. |
| 5,413,559 A | 5/1995 | Sirhan et al. |
| 5,425,712 A | 6/1995 | Goodin |
| 5,441,484 A | 8/1995 | Atkinson et al. |
| 5,445,624 A | 8/1995 | Jimenez |
| 5,447,497 A | 9/1995 | Sogard et al. |
| 5,470,322 A | 11/1995 | Horzewski et al. |
| 5,480,383 A | 1/1996 | Bagaoisan et al. |
| 5,499,973 A * | 3/1996 | Saab ..................... 604/96.01 |
| 5,499,980 A | 3/1996 | Euteneuer |
| 5,507,995 A | 4/1996 | Schweich, Jr. et al. |
| 5,509,899 A | 4/1996 | Fan et al. |
| 5,509,910 A | 4/1996 | Lunn |
| 5,531,719 A | 7/1996 | Takahashi |
| 5,533,985 A | 7/1996 | Wang |
| 5,544,121 A | 8/1996 | Dosaka et al. |
| 5,569,218 A | 10/1996 | Berg |
| 5,622,665 A | 4/1997 | Wang |
| 5,649,909 A | 7/1997 | Cornelius |
| 5,658,263 A | 8/1997 | Dang et al. |
| 5,676,659 A | 10/1997 | McGurk |
| 5,700,252 A | 12/1997 | Klingenstein |
| 5,728,063 A * | 3/1998 | Preissman et al. ..... 604/103.09 |
| 5,728,067 A | 3/1998 | Enger |
| 5,749,849 A | 5/1998 | Engelson |
| 5,755,690 A | 5/1998 | Saab |
| 5,759,173 A | 6/1998 | Preissman et al. |
| 5,759,191 A | 6/1998 | Barbere |
| 5,772,641 A | 6/1998 | Wilson |
| 5,775,327 A | 7/1998 | Randolph et al. |
| 5,800,391 A | 9/1998 | Kontos |
| 5,836,925 A | 11/1998 | Soltesz |
| 5,851,203 A | 12/1998 | van Muiden |
| 5,868,704 A | 2/1999 | Campbell et al. |
| 5,868,706 A | 2/1999 | Cox |
| 5,951,929 A | 9/1999 | Wilson |
| 5,971,975 A | 10/1999 | Mills et al. |
| 5,980,505 A | 11/1999 | Wilson |
| 5,980,530 A | 11/1999 | Willard et al. |
| 5,984,907 A | 11/1999 | McGee et al. |
| 6,004,289 A | 12/1999 | Saab |
| 6,021,340 A | 2/2000 | Randolph et al. |
| 6,030,369 A | 2/2000 | Engelson et al. |
| 6,036,677 A | 3/2000 | Javier, Jr. et al. |
| 6,039,743 A | 3/2000 | Quiachon et al. |
| 6,045,547 A | 4/2000 | Ren et al. |
| 6,059,769 A | 5/2000 | Lunn et al. |
| 6,066,114 A | 5/2000 | Goodin et al. |
| 6,068,634 A | 5/2000 | Lorentzen Cornelius et al. |
| 6,086,556 A | 7/2000 | Hamilton et al. |
| 6,093,177 A | 7/2000 | Javier, Jr. et al. |
| 6,103,037 A | 8/2000 | Wilson |
| 6,106,485 A | 8/2000 | McMahon |
| 6,106,510 A | 8/2000 | Lunn et al. |
| 6,129,708 A | 10/2000 | Enger |
| 6,132,824 A | 10/2000 | Hamlin |
| 6,135,992 A | 10/2000 | Wang |
| 6,136,258 A | 10/2000 | Wang et al. |
| 6,139,525 A | 10/2000 | Davis-Lemessy et al. |
| 6,168,588 B1 | 1/2001 | Wilson |
| 6,179,856 B1 | 1/2001 | Barbere |
| 6,195,969 B1 | 3/2001 | Yilmaz |
| 6,197,015 B1 | 3/2001 | Wilson |

| | | |
|---|---|---|
| 6,200,290 B1 | 3/2001 | Burgmeier |
| 6,217,565 B1 | 4/2001 | Cohen |
| 6,234,995 B1 | 5/2001 | Peacock, III |
| 6,240,231 B1 | 5/2001 | Ferrera et al. |
| 6,273,879 B1 | 8/2001 | Keith et al. |
| 6,299,596 B1 | 10/2001 | Ding |
| 6,319,228 B1 * | 11/2001 | Kastenhofer ............ 604/96.01 |
| 6,319,244 B1 | 11/2001 | Suresh et al. |
| 6,328,731 B1 | 12/2001 | Ouchi |
| 6,355,027 B1 | 3/2002 | Le et al. |
| 6,406,457 B1 | 6/2002 | Wang et al. |
| 6,443,925 B1 | 9/2002 | Schaible et al. |
| 6,465,067 B1 | 10/2002 | Wang et al. |
| 6,482,348 B1 | 11/2002 | Wang et al. |
| 6,503,223 B1 | 1/2003 | Sekido et al. |
| 6,503,353 B1 | 1/2003 | Peterson et al. |
| 6,517,548 B1 | 2/2003 | Lorentzen Cornelius et al. |
| 6,527,789 B1 | 3/2003 | Lau et al. |
| 6,530,938 B1 | 3/2003 | Lee et al. |
| 6,562,021 B1 | 5/2003 | Derbin et al. |
| 6,575,934 B1 | 6/2003 | Duchamp |
| 6,579,277 B1 | 6/2003 | Rabiner et al. |
| 6,589,226 B1 | 7/2003 | Owens |
| 6,648,024 B1 | 11/2003 | Wang |
| 6,663,614 B1 | 12/2003 | Carter |
| 6,702,802 B1 * | 3/2004 | Hancock et al. ............ 604/524 |
| 6,706,010 B1 | 3/2004 | Miki et al. |
| 6,726,714 B1 | 4/2004 | DiCaprio et al. |
| 6,793,634 B1 | 9/2004 | White et al. |
| 6,887,219 B1 | 5/2005 | Wantink |
| 6,942,648 B1 | 9/2005 | Schaible et al. |
| 6,960,188 B1 | 11/2005 | Jörgensen |
| 2001/0021840 A1 | 9/2001 | Suresh et al. |
| 2002/0077654 A1 | 6/2002 | Javier, Jr. et al. |
| 2002/0081406 A1 | 6/2002 | Wang et al. |
| 2002/0156459 A1 | 10/2002 | Ye et al. |
| 2002/0156460 A1 | 10/2002 | Ye et al. |
| 2003/0009129 A1 | 1/2003 | Miller et al. |
| 2003/0083691 A1 | 5/2003 | Wantink |
| 2003/0093059 A1 | 5/2003 | Griffin et al. |
| 2003/0100849 A1 | 5/2003 | Jang |
| 2003/0105426 A1 | 6/2003 | Jorgensen |
| 2003/0139759 A1 | 7/2003 | Schaible et al. |
| 2004/0054323 A1 | 3/2004 | Wantink |
| 2004/0065979 A1 | 4/2004 | Wang |
| 2004/0116901 A1 | 6/2004 | Appling |
| 2004/0210210 A1 | 10/2004 | Quint |
| 2004/0210211 A1 | 10/2004 | Devens, Jr. et al. |
| 2004/0225279 A1 | 11/2004 | Raymond |
| 2004/0236310 A1 | 11/2004 | Chin et al. |
| 2004/0243102 A1 | 12/2004 | Berg et al. |
| 2005/0148997 A1 | 7/2005 | Valley et al. |

FOREIGN PATENT DOCUMENTS

| | | |
|---|---|---|
| WO | WO00/45885 | 8/2000 |
| WO | WO01/32398 | 5/2001 |
| WO | WO01/43944 | 6/2001 |
| WO | WO02/36194 | 5/2002 |

OTHER PUBLICATIONS

List of References [online], 7 pages Retrieved from the Thomson Derwent World Patent Index.

* cited by examiner

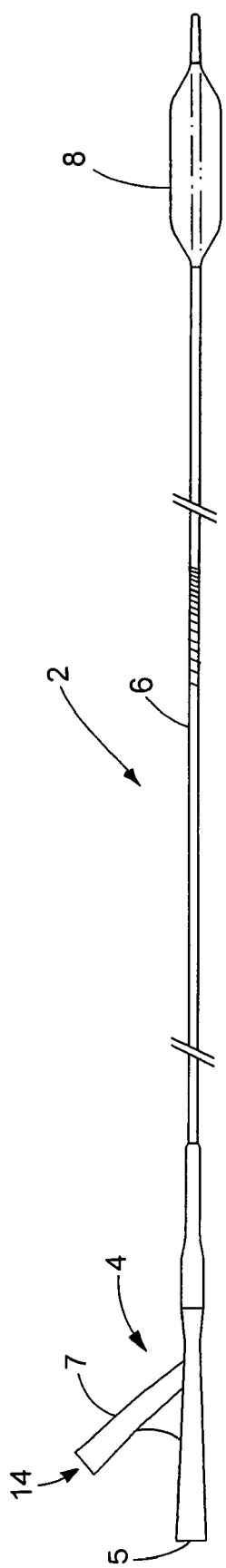
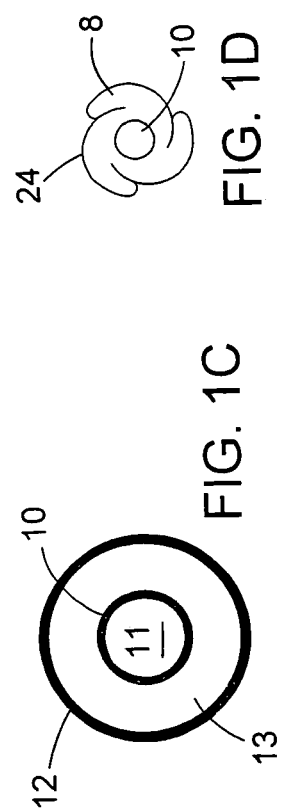
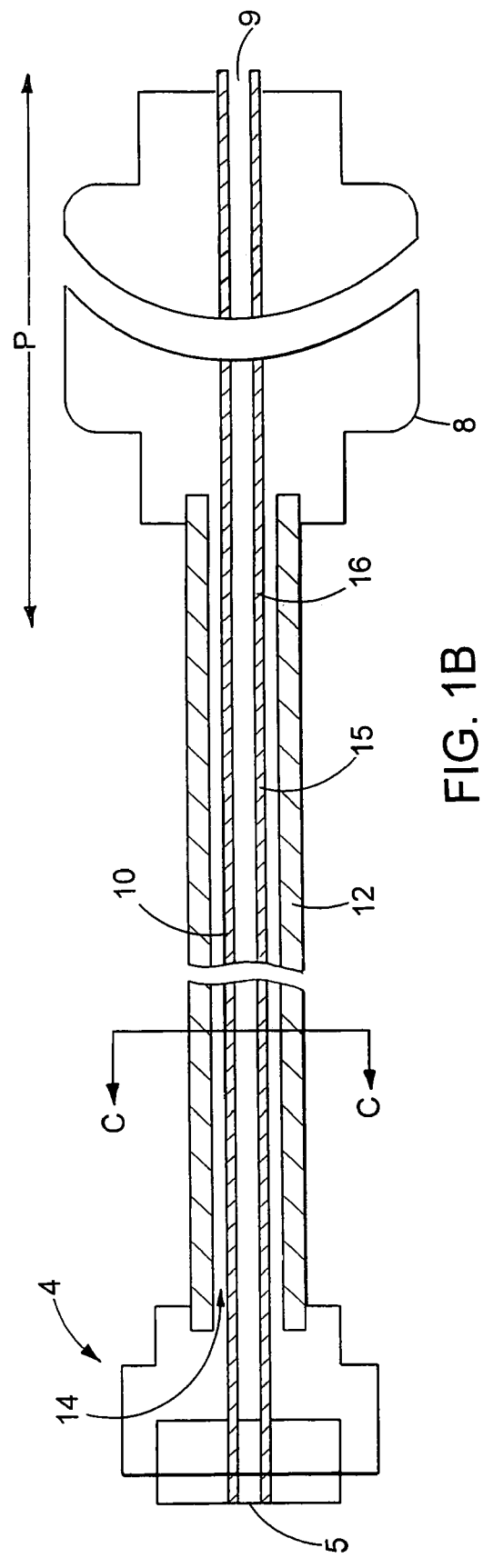
FIG. 1A
FIG. 1B
FIG. 1C
FIG. 1D

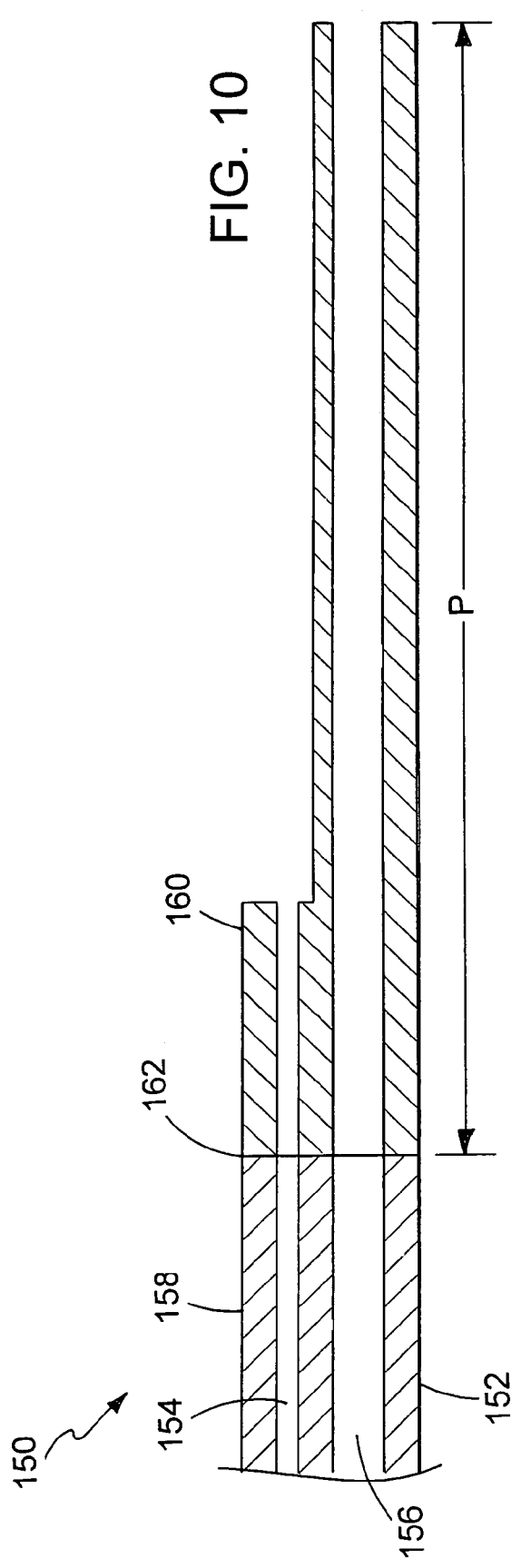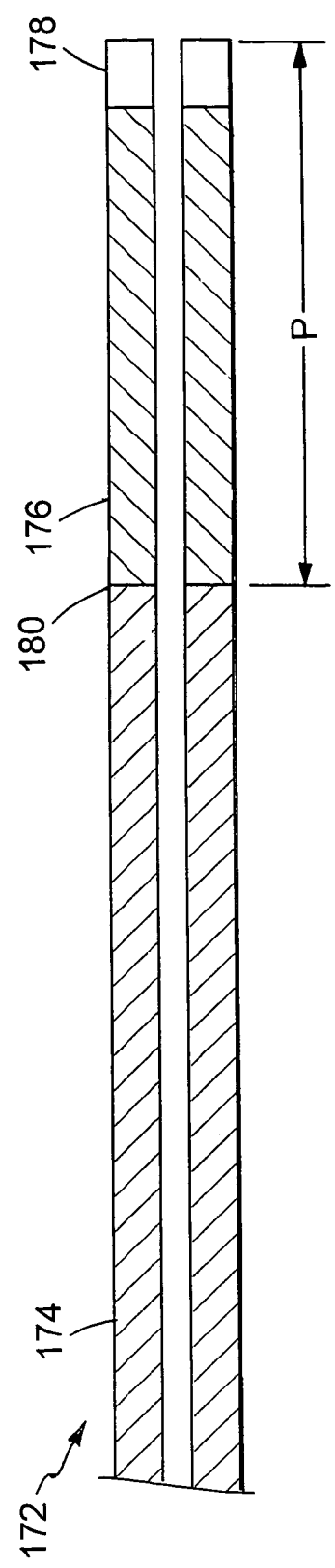

BALLOON CATHETER

CROSS REFERENCE TO RELATED APPLICATION

This application claims the benefit of the filing date of U.S. Provisional Application No. 60/450,255, filed Feb. 26, 2003.

TECHNICAL FIELD

This invention relates to balloon catheters.

BACKGROUND

The body includes various passageways such as arteries, other blood vessels, and other body lumens. These passageways sometimes become occluded by a tumor or restricted by plaque. To widen an occluded body vessel, balloon catheters can be used, for example, in angioplasty.

A balloon catheter can include an inflatable and deflatable balloon carried by a long and narrow catheter body. The balloon is initially folded around the catheter body to reduce the radial profile of the balloon catheter for easy insertion into the body.

During use, the folded balloon can be delivered to a target location in the vessel, e.g., a portion occluded by plaque, by threading the balloon catheter over a guide wire emplaced in the vessel. The balloon is then inflated, e.g., by introducing a fluid into the interior of the balloon. Inflating the balloon can radially expand the vessel so that the vessel can permit an increased rate of blood flow. After use, the balloon is deflated and withdrawn from the body.

In another technique, the balloon catheter can also be used to position a medical device, such as a stent or a stent-graft, to open and/or to reinforce a blocked passageway. For example, the stent can be delivered inside the body by a balloon catheter that supports the stent in a compacted or reduced-size form as the stent is transported to the target site. Upon reaching the site, the balloon can be inflated to deform and to fix the expanded stent at a predetermined position in contact with the lumen wall. The balloon can then be deflated, and the catheter withdrawn.

One common balloon catheter design includes a coaxial arrangement of an inner tube surrounded by an outer tube. The inner tube typically includes a lumen that can be used for delivering the device over a guide wire. Inflation fluid passes between the inner and outer tubes. An example of this design is described in Arney U.S. Pat. No. 5,047,045, the entire contents of which is hereby incorporated by reference.

In another common design, the catheter includes a body defining a guide wire lumen and an inflation lumen arranged side-by-side. Examples of this arrangement are described in Wang U.S. Pat. No. 5,195,969 the entire contents of which is hereby incorporated by reference.

SUMMARY

In aspects, the invention features a balloon catheter including a tubular member that has a first proximal section and a second, distal section and a transition, the second section having a column strength less than a column strength of the first section and one or more of the features described herein.

In an aspect, the invention features a concentric balloon catheter, having a polymeric outer tubular member, including a balloon and a polymeric inner tubular member. The inner tubular member has a first, proximal section, a second more distal section, and a transition. The second section has a column strength and/or flexural modulus of about 75% or less than the column strength of the first section. The transition is located, e.g., about 1 to 10 cm, about 2 to 9 cm, about 4 to 8 cm from the distal end of the inner tubular member.

In another aspect, the invention features a concentric vascular angioplasty balloon catheter that includes an outer tubular member defining a lumen. A balloon is attached to the outer tubular member. The catheter also includes an inner tubular member comprising multiple layers located within the lumen of the outer tubular member. The inner tubular member has a first, proximal section welded to a second, more distal section to define a transition located proximal of the balloon. The inner tubular member has three or more layers in each of the first and second sections and the second section has a column strength less than a column strength of the first section.

In another aspect, the invention features a balloon catheter having a tubular member, a first lumen for delivery over a guidewire and a second lumen for communicating inflation fluid to the balloon. The tubular member also has a first proximal section, a second, distal section and a transition. The second section has a column strength, per unit length, less than the column strength, per unit length, of the first section and the transition is located about 1.0 cm or more from the distal end of the tubular member. The tubular member exhibits improved trackability, e.g. 10, 20, or 30 percent or more improved trackability, when compared to a monolithic tubular member having a column strength intermediate to the column strength of the first and second sections.

Embodiments may include one or more of the following. The transition is in the range of about 1 to about 10 cm (e.g., about 3 to about 8 cm, about 4 to about 7.5 cm, about 4 to about 7 cm) from the distal end of the inner tubular member. A distance measured from the transition to a distal end of the inner tubular member is no more than about 20 percent (e.g., no more than about 5 percent) of an overall length of the inner tubular member. The first section has a column strength, per 2.54 cm, of about 5 g to 20 g and the second section can have a column strength of about 2 to 7 g. The second section has a flexural modulus of about 75 percent or less (e.g., between about 20 and 40 percent) of a flexural modulus of a flexural modulus of the first section. The location of the transition is located proximal of the balloon. The balloon is between about 8 and 40 millimeters in length, the balloon has an inflated diameter of between about 1.5 and 10 millimeters, and/or the balloon includes polyethylene terethalate or nylon. The transition can also be located at a joint between the first and second tube sections. Trackability can be measured by push response, track force and/or input force.

Embodiments may also include one or more of the following. The transition includes a thickness variation of a first polymer and a second polymer. The transition includes a variation in diameter of the tubular member such as the first and second sections having different diameters. Where the first and second sections have different diameters, the sections can have the same polymer composition. The first and second sections of the catheter can also have different polymer compositions.

Embodiments may include one or more of the following. The catheter has at least one of the first and second sections include multiple layers, including an inner most layer. These multiple layers can include at least two layers (e.g., 3 or more layers). The outermost layers of the first and second sections are formed of different polymers and the other layers of the first and second sections are formed of the same polymer. The outermost layer of the first section is formed of nylon and/or the outermost layer of the second section is formed of polyether-block co-polyamide. The first and second sections can have the same innermost layer, e.g., formed of polyethylene. In other words, the inner most layer of the two sections can be the same material throughout. A second layer in both the proximal and distal sections can be elastomeric. The catheter can be a vascular angioplasty catheter. The first and second lumens of the catheter can be arranged side-by-side in a tubular body. The first and second lumens can be concentric. The outer tubular member is of a monolithic polymer construction, for example, formed of polyamide.

Embodiments may include one or more of the following advantages. A catheter having enhanced deliverability can be provided. The catheter can accommodate a gradual unfolding of a balloon, and hence a corresponding variation in stiffness near the distal end of the catheter, as the catheter is delivered into a tortuous lumen. The buckling strength of proximal and distal sections along the catheter length can be selected to provide sufficient pushability, so that the catheter can be urged distally from its proximal end, and sufficient trackability, so that the catheter can be guided along a tortuous path over a guide wire. The sections can be characterized by, for example, their column strength and/or flexural modulus. The sections can be tubes made of multiple polymer layers that provide advantages such as high collapse resistance and low friction lumen walls. The outer layer of the multi-layer structure can be a highly elastic polymer, such as an elastomer. The multilayer tubular member can have a substantially constant outer diameter along its length. Alternatively, the diameter can vary. The thickness of each of the layers can be selected to affect catheter performance.

The details of one or more embodiments of the invention are set forth in the accompanying drawings and the description below. Other features, objects, and advantages of the invention will be apparent from the description and drawings, and from the claims, including methods of manufacture and use.

DESCRIPTION OF DRAWINGS

FIG. 1A is a side view of a balloon catheter.

FIG. 1B is an axial cross-sectional view of the balloon catheter in FIG. 1A.

FIG. 1C is a cross-sectional view along line CC of FIG. 1B.

FIG. 1D is a cross-section through the balloon with the balloon in a deflated state.

FIG. 10 is a cross-section of a balloon catheter.

FIG. 11 is a cross-section of a balloon catheter.

Like reference symbols in the various drawings indicate like elements.

DETAILED DESCRIPTION

Figures 2A, 2B:
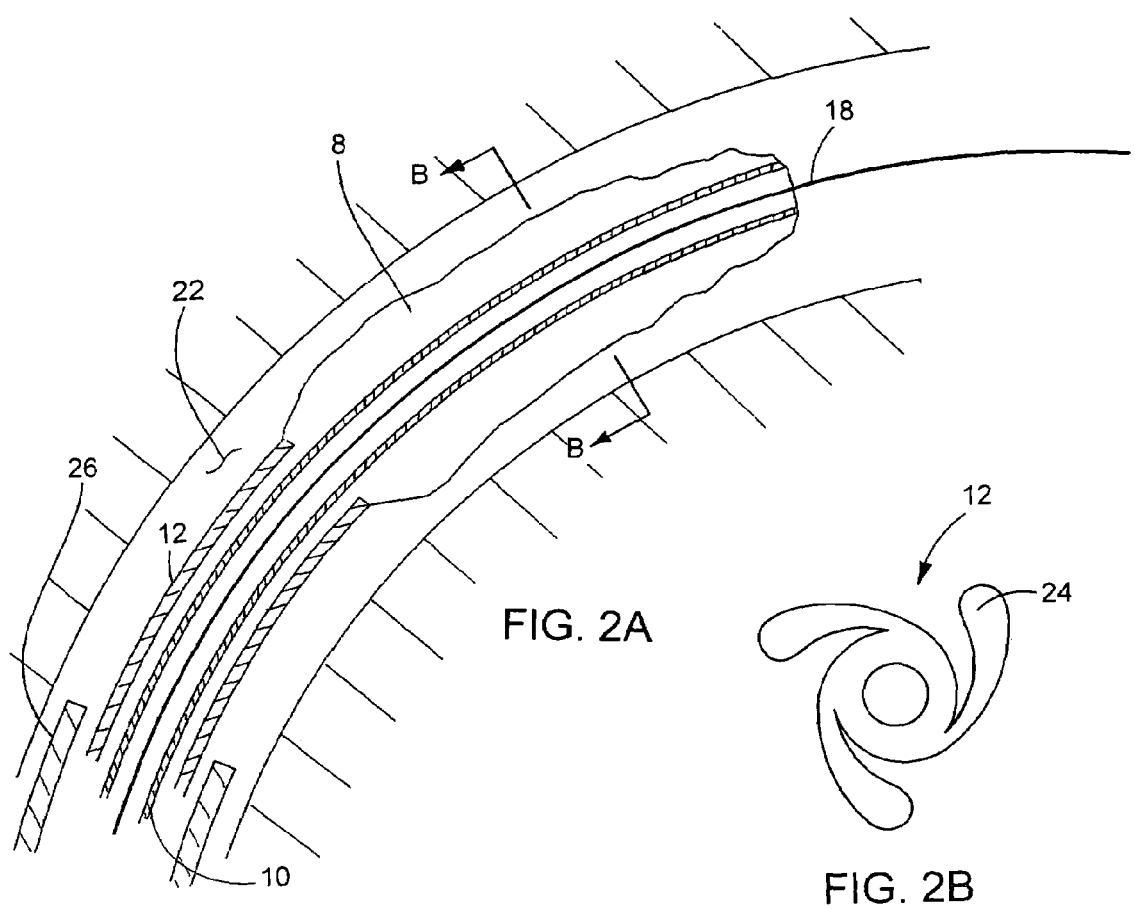
FIG. 2A is a cross-sectional view of a balloon catheter in a body lumen.
FIG. 2B is a cross-sectional view along line BB of FIG. 2A.

Referring to FIG. 1A, a balloon catheter 2 includes a proximal portion 4, and a distal portion that has a flexible body 6 and an inflatable balloon 8. The proximal portion 4, which remains outside the patient, includes a guide wire port 5 and an inflation fluid port 7. Referring particularly to FIGS. 1B and 1C, the catheter 2 has a coaxial design including an inner tube 10 and a coaxially arranged outer tube 12. The inner tube 10 defines between a proximal opening 7 and a distal opening 9, a lumen 11 which extends the length of the tube 10 so that the catheter can be delivered over a guide wire. The inner tube 10 has a proximal section 15, a second distal section 16, and a transition 17 between the sections. The flexibility of the sections and the position, P, of the transition between the sections is selected to enhance deliverability of the catheter, as will be described in detail below.

The outer tube 12 extends from the proximal end to the balloon 8. A lumen 13 is defined between the inner tube 10 and the outer tube 12 through which inflation fluid can be delivered (arrows 14). The balloon 8 is attached at its proximal end to the outer tube 12 and at its distal end to the inner tube 10. Referring to FIG. 1D, prior to delivery into a body lumen, the balloon 8 is typically maintained in a low-profile configuration by tightly wrapping the balloon 8 around the inner tube in a series of overlapping wings or folds 24.

In embodiments, the distal portion of the catheter has a length of about, e.g., 60 to 140 cm. The balloon has an inflated diameter of about 1.5 to 10 mm, a length of about 8 to 40 mm and can include a relatively stiff, noncompliant material such as a biaxially oriented polymer, e.g. PET or nylon. The balloon can also be formed of compliant or semi-compliant materials such as PEBAX, available from Atofina, Philadelphia, Pa., as an example. The outer tube is a relatively stiff, burst-resistant polymer such as polyamide-12. Typically, the catheter inner tube has an overall length of about 25 cm to 140 cm, but can be longer or shorter depending on the application. For example, in coronary applications, the catheter typically has an overall length sufficient to be delivered femorally, via the femoral artery, or brachially, via the brachial artery. The catheter can also be delivered peripherally, for example, via the radial artery. For vascular applications, the length is typically about 135 to 140 cm. The catheter can be a rapid exchange type catheter in which the guidewire exits the guidewire lumen distal of the proximal portion 4.

Referring to FIG. 2A, the catheter 2 is delivered into a body lumen 22 over a guide wire 18. The catheter may be delivered through an introducer 26, also positioned in the lumen. The exit of the introducer may be positioned at a point proximal of a region of lumen tortuosity or reduced diameter, e.g., in the coronary artery. The catheter 2 is extended from the end of the introducer to position the balloon at a treatment site where the balloon is inflated to dilate the lumen. For example, in coronary applications, the distal end of the catheter typically extends from about 1 to 15 cm from the end of the introducer in delivering the balloon to the treatment site.

Referring also to FIG. 2A, as the catheter is urged through the body lumen 22, balloon 8 becomes partially unfolded thus increasing the diametric profile of balloon 8 and also modifying the flexibility profile of the catheter. In particular, when the balloon is tightly wrapped about a catheter (FIG. 1D), the stiffness of the distal portion of the catheter is largely influenced, or even dominated, by the balloon. However, as the catheter is delivered into the body through the introducer, and particularly as the distal portion of the catheter extends beyond the introducer, the balloon wrapping loosens, as illustrated in FIG. 2A. The mechanical characteristics of the catheter becomes increasingly influenced, even largely dominated, by the inner tubular member. When the catheter is used to deliver a stent, the stent is slipped over the balloon after the balloon has been tightly wrapped about the catheter body. The stent can be held in place by partially inflating the balloon, which loosens the wrapped configuration of the balloon.

The catheter deliverability is enhanced by selecting in combination the relative buckling strength of the proximal and distal sections of the inner tube and the location of the transition between the sections. The buckling strength of the proximal and distal sections can be determined by measuring the column strength and/or flexural modulus of the sections. The position of the transition is measured from the distal end. The buckling strength differences and position of the transition are selected to balance the catheter pushability and trackability. Pushability is the capability to transmit to the distal end of the catheter an axial or rotational force imposed on the proximal end of the catheter. Trackability is the capability to pass a torturous passageway. Trackability is generally facilitated by a more flexible catheter but too much lateral flexibility can lead to problems such as buckling as the catheter is directed around a sharp curvature.

In a typical application, the performance requirements for deliverability become more severe as the catheter is urged more deeply into a vessel. Greater pushability is required since the distance between the more proximal portion, which is grasped by the physician, and the distal end increases. At the same time, in more remote portions of the vessel, the vessel diameter typically narrows and the vessel becomes more tortuous, thus greater trackability is also desirable.

In embodiments, the column strength and/or flexural modulus of the distal section is about 75% or less, e.g. 40%–20%, than the column strength and/or flexural modulus of the proximal section. The transition is located from the distal end at a position corresponding to about 20% or less, e.g. 10% or 5% or less, than the overall length of the tube. In embodiments, the column strength (measured per 2.54 cm length) of the proximal section is in the range of about 1 to 20 g, e.g., about 2 to 17 g. In embodiments, the column strength (measured per 2.54 cm length) of the distal section is in the range of about 2–7 g and the column strength of the proximal portion is in the range of about 9 to 16 g. In embodiments, the transition is about 1 to 10 cm, e.g., 1.5 to 9 cm, 3 to 8 cm, 4 to 7.5 cm, or 7 cm or less from the distal end of the catheter. The position of the transition can be varied depending on the length of the balloon. The transition is typically under or proximal of the balloon. For a longer balloon, the transition position is generally further from the distal end of the catheter. The transition is typically not so far proximal of the balloon that the unwrapped balloon does not influence the stiffness of substantially the length of the distal section. For example, the transition is typically within about 5 cm or 2 cm or less of the most proximal inflated portion of the balloon. (The most proximal inflated portion is distal of the region where the balloon is attached to the catheter.) In addition, the location of the transition can be selected such that the transition does not substantially extend beyond an introducer. A catheter and introducer can be provided as a kit such that the transition permits a range of catheter extensions without the transition extending beyond the introducer.

Figure 3:
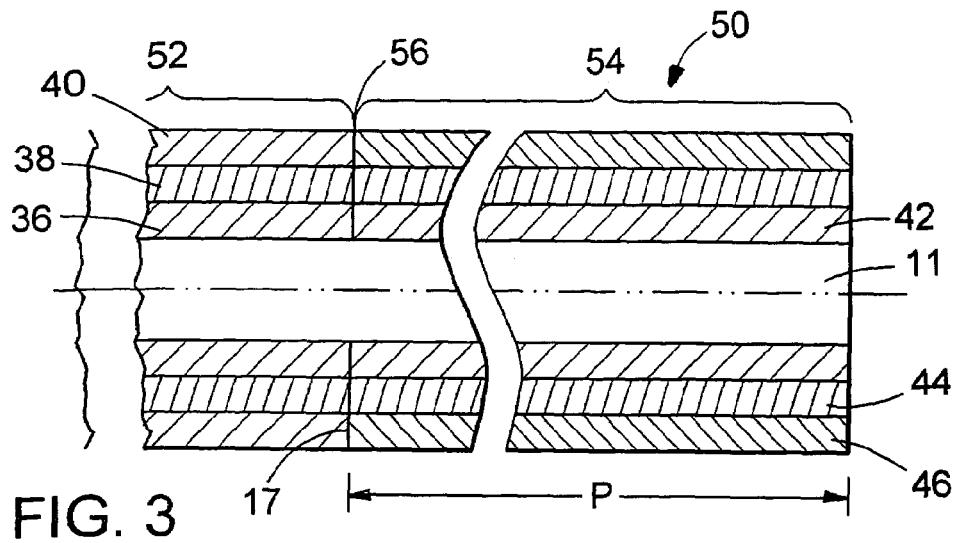
FIG. 3 is a longitudinal cross-sectional view of a tube.

Referring particularly to FIG. 3, in an embodiment, an inner tube 50 includes multiple polymer layers to enhance deliverability and other characteristics. The inner tube 50 includes proximal section 52, distal section 54, and transition 56 selected to enhance delivery through a tortuous lumen. In this example, both sections include multiple, in this case three, layers. The proximal section 52 has an innermost (or inside) layer 36, a middle layer 38, and an outer layer 40. The distal section has an inside layer 42, a middle layer 44, and an outer layer 46. In both the proximal and distal portions, the inside layers 36, 42 are formed of high radial strength, hard, low-friction polymer that resists collapse during balloon inflation and facilitates movement of the catheter over a guide wire. Suitable polymers include high density polyethylenes, fluoropolymers such as ethylene tetrafluoro ethylene, or graphite-filled nylons. A particular high density polyethylene example is Marlex 4903, available from Chevron Phillips. The middle layers 38, 44 are tie layers that facilitate bonding between the inner and outer layers. Suitable polymers include maleic anhyride functionalized linear low-density polyethylenes. A particular example is Plexar PX-380, available from Equistar, Houston, Tex.

The outer layers 40, 46 of the inner tube can be selected to balance pushability and trackability. The outer layer 40 in the proximal section is typically a stiffer material than the outer layer 46 of the distal section 16. The layers 40, 46 meet at a transition 56 at a position, P, from the distal end of the tube. In embodiments, the flexural modulus of the layer 46 is about 75% or less than the flexural modulus of the layer 40. In embodiments, the flexural modulus of the layer 46 is about 15 to 500 MPa and the flexural modulus of the layer 40 is about 700 to 4000 MPa. Suitable polymers include elastomers, such as thermoplastic elastomers. Examples include nylons such as nylon 12. In a particular example, the proximal outer layer 40 is a blend of 60% TR55LX amorphous polyamide 12 available from EMS, Switzerland (flexural modulus of 2000 MPa) and 40% L20 polyamide 12 also available from EMS, Switzerland (flexural modulus of 1100 MPa). The flexural modulus of the blend is about 1600 MPa. The distal outer layer 46 is a blend of 75% Pebax 7033 available from Atofina, Philadelphia, Pa. (flexural modulus of 465 MPa) and 25% Pebax 5533 available from Atofina, Philadelphia, Pa. (flexural modulus of 201 MPa). The flexural modulus of the blend is about 400 MPa. The tube can be manufactured by separately coextruding tube elements for the proximal and distal portions, cutting the tube elements to desired lengths, and bonding the tube elements by comelting with a laser.

Figure 4:
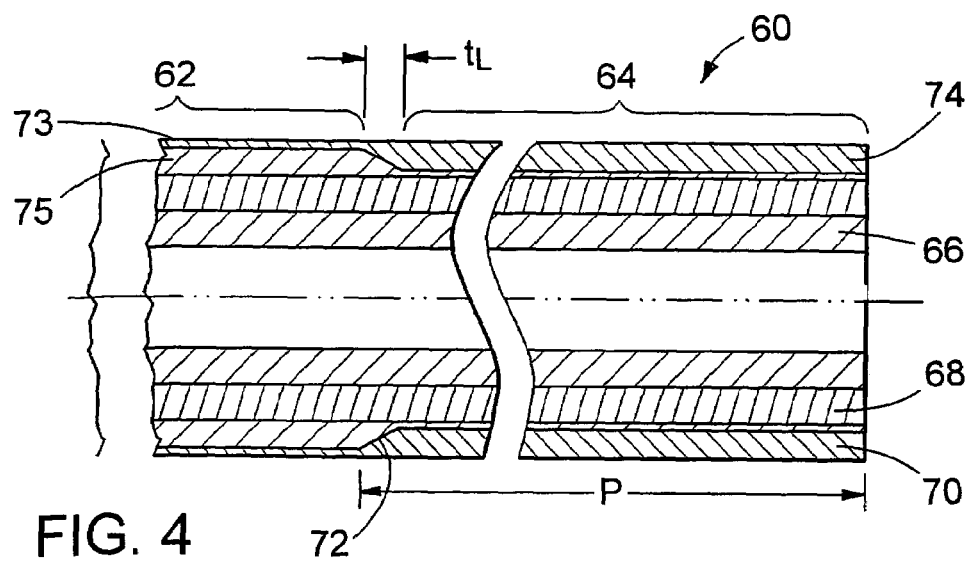
FIG. 4 is a longitudinal cross-sectional view of a tube.

Referring to FIG. 4 in another embodiment, a multilayer inner tube 60 is made by a continuous coextrusion process that defines a tube of substantially constant diameter. The tube 60 includes a proximal section 62 and a distal section 64 having three layers. Inside layer 66 is made of material that provides low friction between the inside layer 66 and a guide wire (not shown) as the catheter tracks along the guide wire within the body lumen. Middle layer 68 is a bonding agent, bonding the inside layer 66 and an outer layer 70. The outer layer is selected to alter flexibility relative to a transition region 72. The inner and middle layers are generally of constant thickness.

The outer layer is composed of two sublayers 73, 75. In the proximal section, the layer 73 is relatively thin and the layer 75 is relatively thick. In the distal section, layer 73 is relatively thin and the layer 75 is relatively thick. The column strength or flexural modulus of the materials in layers 73, 75, the relative thickness of the layers, and the transition 72 can be varied. For example, in the example illustrated, the material in layer 73 may have a greater flexural modulus than the material in layer 75. In this arrangement, the transition 72 has a transition length $t_L$ over which the thickness of sublayers 73, 75 varies. The flexibility in the transition varies. The transition position, P, is measured from the distal end of the tube to the middle of the transition length $t_L$. In embodiments in which a variation in relative thickness of the sublayers extends to the distal end, the transition length is measured at the middle of the transition. The tube can be made by coextrusion. Coextrusion is described in WO 01/32398A1, which is incorporated herein by reference.

Figure 5:
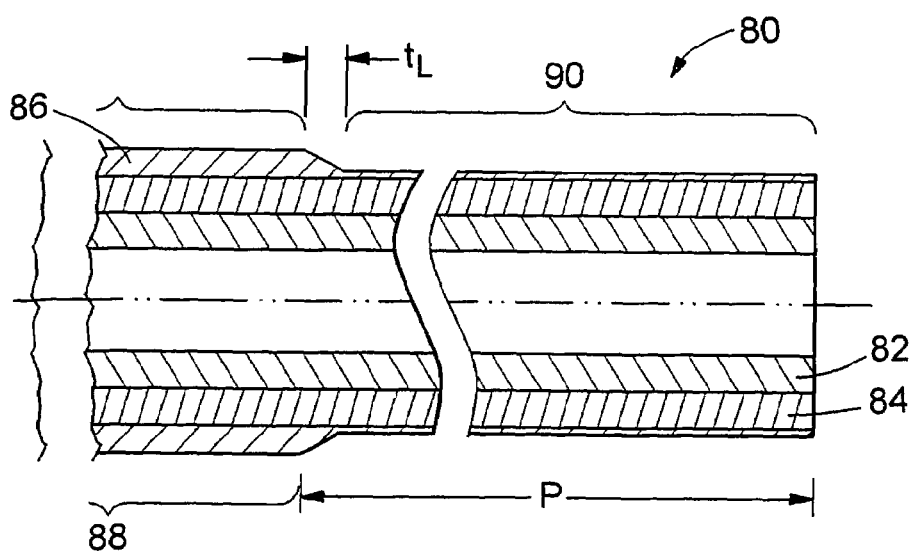
FIG. 5 is a longitudinal cross-sectional view of a tube.

Referring now to FIG. 5, in another embodiment, a tube 80 has proximal and distal sections of different dimensions. Tube 80 has a proximal section 88, a distal section 90, and a transition 92. The tube portions have three layers with an inside layer 82 of a constant material and constant cross section. Middle layer 84 is a bonding layer, also of constant material and constant cross section. Middle layer 84 bonds the inside layer 82 and a cover layer 86. The outer diameter from the larger outer diameter proximal section 88 tapers to the smaller diameter distal section 90. The transition 92 has a transition length $t_L$ where the thickness of the tube varies. The tube is formed by coextrusion. The diametric variation is formed by varying the puller speed during coextrusion. This varying of puller speed creates a transition region 92 where the larger outer diameter of the proximal section 88 tapers to the smaller outer diameter of the distal section 90.

EXAMPLES

Column Strength and Flexural Modulus Measurements

Figure 6:
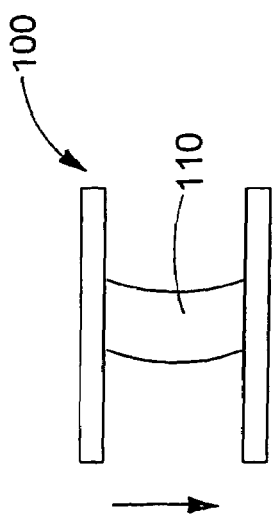
FIG. 6 illustrates a column strength test.

Column strength can be measured by investigating load before buckling. Referring to FIG. 6, an Instron 100 is used, having a 50 N load cell traveling at 1 inch per minute, to measure the buckling strength of a 1-inch (2.54 cm) long tube sample 110. The column strength is taken as the peak load measured prior to buckling. A suitable instrument is a Bionix® 100, available from MTS Systems Corporation. The flexural modulus, which represents the ratio of stress to strain as a material is deformed under dynamic load, can be measured by ASTM method D790, the entire contents of which is incorporated herein by reference.

Push Strength and Track Force

Figure 7:
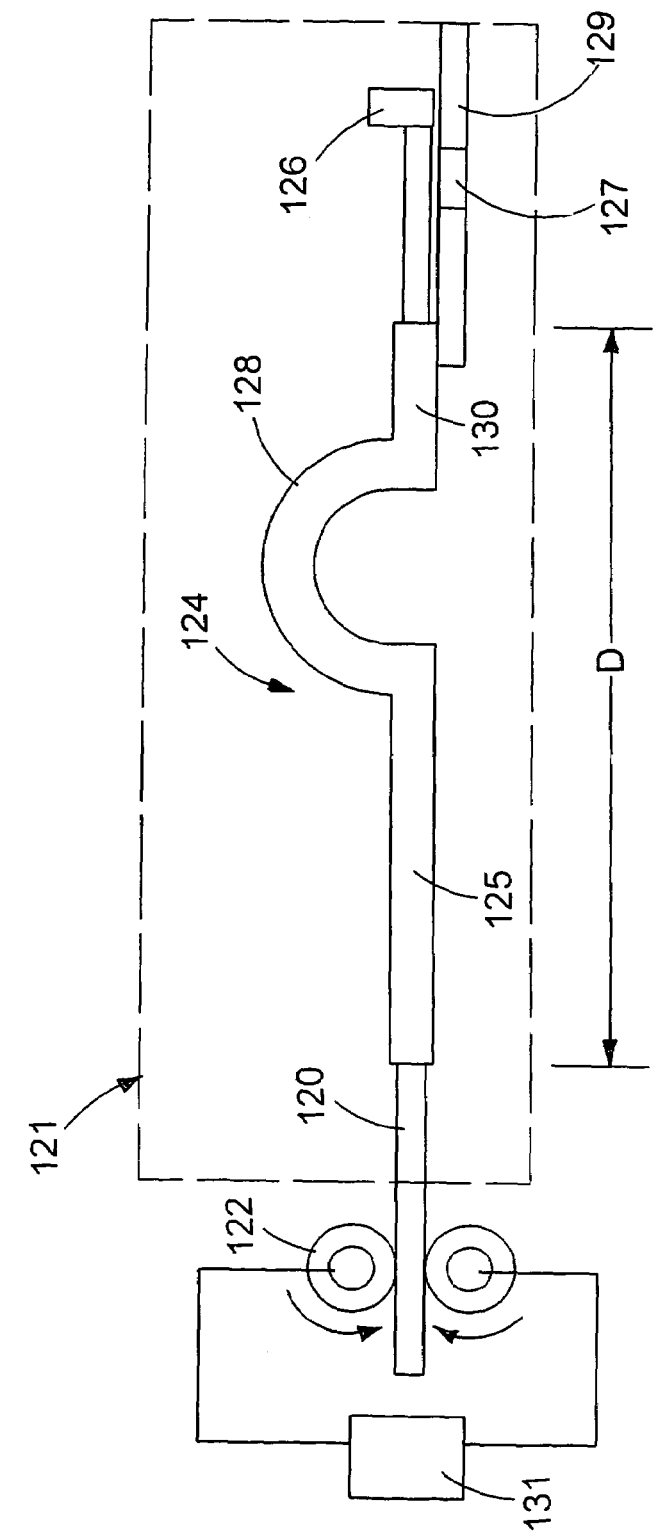
FIG. 7 illustrates push strength and track response tests.

Referring to FIG. 7, deliverability comparisons of catheters can be made using a test assembly that has a tortuous path 124 defined by a polymer tube. Forces on the catheter and the tube can be measured by a series of transducers 126, 127, 131. Push response is measured at transducer 126 by threading the catheter through the path such that the distal end abuts the transducer. As a force is imposed on a proximal portion of the catheter by a pair of drive wheels 122, the transducer 126 measures the amount of force that is transferred from the proximal to the distal end. Track force is measured by transducer 127 as a function of catheter location along the path as the catheter is driven through the path at a constant rate. The transducer 127 measures the deflection of a base 129 from which the tube is cantilevered. By measuring the deflection of the base, the force on the path as the catheter is threaded along can be determined. Input force is the force measured by transducer 131. Transducer 131 measures the force required to drive the catheter along the path at a constant rate as a function of distance of catheter travel. The track force data and input force data can be integrated to determine the total work required to deliver samples along the path.

A suitable path 124 is defined in a tube element made of Teflon™, which has an inner diameter of 0.074 inch, and a wall thickness of 0.006 inch. The path has an overall length of about 13.25 inch. The path has a first straight leg 125 of 11.25 inch, a 1.5 inch diameter semicircular bend 128 and a second straight leg 130 of 0.5 inch. A 0.014 inch diameter guide wire is positioned in the path. A tortuous path 124 mimics the path found in the coronary arteries. Entrance of a test sample into the tortuous path 124 simulates the exiting of the distal end of the catheter from the introducer into the path defined by the exposed artery (see FIG. 2A). The path is immersed in a water bath at 37° C. A suitable drive speed is about 20 cm/min.

Tube Data

Referring to Table I, column strength and push response data for several tube samples is provided.

TABLE I

| Sample | Tube Design | Transition Position | Column Strength | Push response |
|---|---|---|---|---|
| 1 | Polyamide MA/PE PE | — | 13 g | — |
| 2 | Pebax blend MA/PE PE | — | 4.5 g | — |
| 3 | ½ | 5 cm | — | 23 g/cm |
| 4 | ½ | 7 cm | — | 19 g/cm |
| 5 | Pebax MA/PE PE | — | 5.7 g | 19 g/cm |
| 6 | Polyamide MA/PE PE (0.0235 in) | — | 8.4 g | — |
| 7 | Polyamine MA/PE PE (0.022 inch) | — | 5.9 g | — |
| 8 | 6/7 | 5 cm | — | 24 g/cm |

In Samples 1 and 2, proximal and distal inner tube sections are formed by coextrusion. The tubes are extruded with an inner diameter equal to about 0.017 inches and an outer diameter equal to about 0.022 inches. The proportional thickness for each of the three layers is 0.8:0.4:1 for the inside, middle and cover layers, respectively. In both the proximal and distal sections, the inside layer is PE (Marlex 4903) and the middle layer is Plexar PX-380. The proximal section (Sample 1) of the outer layer is a pellet mixed blend of 60% TR55LX amorphous polyamide 12 and 40% L20 polyamide 12. The distal section of the outer layer is a pellet mixed blend of 75% Pebax 7033 and 25% Pebax 5533. After forming the proximal and distal three-layer sections, each is tested to determine their respective column strengths. As the table indicates, the column strength of the distal section (Sample 2) was about 35% of the column strength of the proximal section (Sample 1).

In Sample 3, a two section tube is prepared by laser welding squared ends of the proximal and distal sections described in Samples 1 and 2 to form a bi-component inner tube. (As used herein, "bi-component" refers to an inner tube having a transition as described above. The term "monolithic" refers to an inner tube having no transition (e.g., an inner tube of constant coextrusion).) The end of the distal section is then trimmed to a length of 5 cm (this distance being the transition position P measured from the distal end). As the table indicates, the bi-component tube in Sample 3 has a push response of about 23 g/cm. In Sample 4, the tube structure is the same as in Sample 3 but the transition is at 7 cm. The push response is about 19 g/cm.

In Sample 5, an inner tube is formed by constant coextrusion with no transition (i.e., the inner tube is monolithic). The outer layer of the tube is Pebax 7233 and the middle layer and inside layer are Plexar PX-380 and Marlex 4903, respectively. The column strength is 5.7 g, intermediate between the proximal and distal portions in Samples 1 and 2. In Sample 5, the push strength is 19 g/cm, which is about 18% less than the push strength of Sample 3. Thus, bi-component Sample 3 exhibits an improved push strength relative to monolithic Sample 5.

In Samples 6–8, tubes having varying dimensions are investigated. In Sample 6, a monolithic tube component is extruded to have three layers. The outer layer is L20 polyamide 12 and the inside and middle layers are Marlex 4903 and Plexar PX-380, respectively. Sample 7 is also a monolithic tube component formed of an outer layer of L20 polyamide 12, a middle layer of Plexar PX-380 and an inside layer of Marlex 4903. Each of the layers of the Samples 6 and 7 are of constant wall thickness, but the outer diameter of Sample 7 is less than the outer diameter of Sample 6. Sample 6 has an outer diameter of 0.0235 inch and Sample 7 has an outer diameter of 0.021 inch. The column strength of Sample 6 is 8.4 g and the column strength of Sample 7 is 5.9 g.

Sample 8 combines Samples 6 and 7 by tapering the outer layer of L20 polyamide 12, from the proximal outer diameter of 0.0235 inch to a smaller distal diameter of 0.021 inch a position (P) 5 cm from the distal end. The outer layer diameter is tapered by varying the puller speed during coextrusion. The inner tubular member is tested as outlined above. As the data indicates, Sample 8 exhibits a push response of about 24 g/cm.

Referring now to Table II, track work data is provided for a series of coaxial catheters using inner tubes of different designs.

TABLE II

| Sample | Inner Tube Design | Transition Location | Track Work (g-cm) |
|---|---|---|---|
| Monolithic Sample 1 | Pebax 7233 (outer) MA/PE (middle) PE (inside) | none | 121.2 |
| Bi-component Sample 1 | Polyamide (proximal outer) Pebax blend (distal outer) MA/PE (middle) PE (inside) | 7 cm | 99.9 |
| Bi-component Sample 2 | Pebax 7233 (proximal outer) Pebax 63D (distal outer) MA/PE (middle) PE (inside) | 7 cm | 93.2 |
| Bi-component Sample 3 | Pebax 7233 (proximal outer) Pebax 66D (distal outer) MA/PE (middle) PE (inside) | 7 cm | 95.3 |

To obtain comparative track, the inner tube designs were combined with an outer tube and balloon of common design to provide a catheter assembly. The outer tube included a hypotube of stainless steel that has a length of about 40 inches, an inner diameter of about 0.019 inch and an outer diameter of about 0.023 inch. Laser welded to the distal end of the hypotube is a second tubular section. The second tubular section is made of Pebax 72D, which extends about 15 inches and has an outer diameter of about 0.032 inch and has an inner diameter of about 0.026 inch. The balloon is attached at the distal end at the second tubular section.

Monolithic Sample 1 is a catheter assembly including an inner tube that is a monolithic, three layer extrusion including Pebax 7233 as the outer layer, Marlex 4903 as the middle layer and Plexar PX-380 as the inside layer.

Bi-Component Sample 1 includes an inner tube that has three layers and proximal and distal sections. The proximal section has an inside layer of PE (Marlex 4903), a middle layer of Plexar PX-380 and a outer layer (proximal outer) of a pellet mixed blend of 60% TR55LX amorphous polyamide 12 and 40% L20 polyamide 12. The distal section includes an inside layer of PE (Marlex 4903), a middle layer of Plexar PX-380 and a outer layer (distal outer) of a pellet mixed blend of 75% Pebax 7033 and 25% Pebax 5533. The proximal and distal sections are joined by welding.

Bi-Component Sample 2 has three layers and a proximal and distal section. Inside and middle layers are formed of Marlex 4903 and Plexar PX-380, respectively. The outer layer in the proximal section (proximal outer) is Pebax 7233. The outer layer in the distal section is Pebax 63D.

Bi-Component Sample 3 has three layers and a proximal and distal section. Inside and middle layers are formed of Marlex 4903 and Plexar PX-380, respectively. The outer layer in the proximal section (proximal outer) is Pebax 7233. The outer layer in the distal section is Pebax 66D. The transition region of each of the three bi-component samples is located 7 cm from the distal end.

As the data indicates, the bi-component samples required substantially less work, and hence improved trackability compared to the monolithic samples. In addition, Bi-component Sample 1, which corresponds to Sample 4 in Table I, illustrates improved trackability while maintaining push response of certain monolithic samples, translating to improved deliverability.

Figure 8:
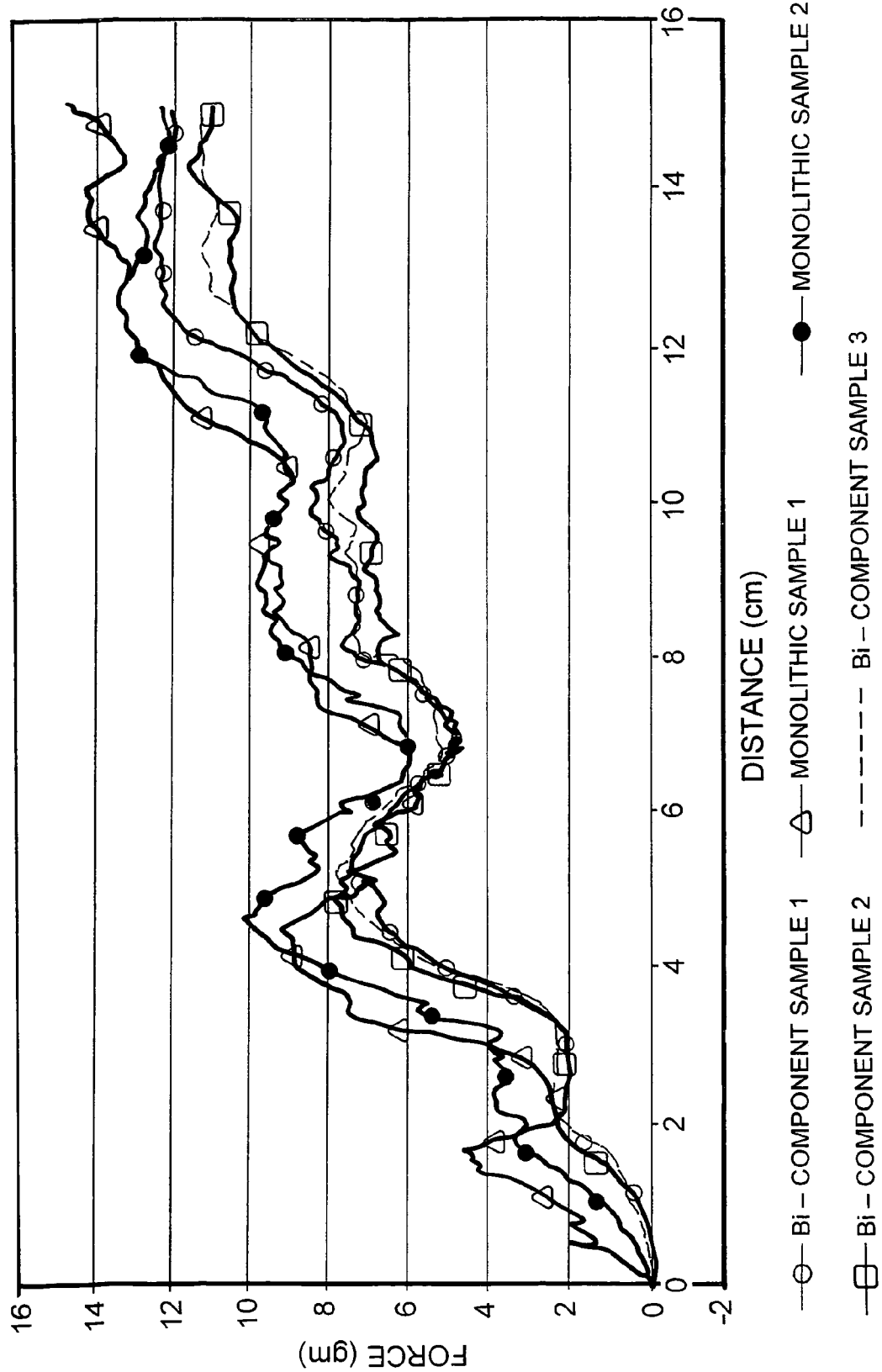
FIG. 8 is a graph of force as a function of distance along a track.

Referring now to FIG. 8, a graph of track force as a function of distance, indicating deliverability, is provided for the assemblies in Table II. The average force per unit distance is less for the bi-component assemblies compared to the monolithic assemblies. For the bi-component samples, the proximal section begins to track through the tortuous path at 7 cm. However, the bi-component samples continue to exhibit improved deliverability relative to the monolithic samples, even beyond 7 cm.

Referring now to Table III, data for catheter assemblies with bi-component samples having inner tubes having different transition locations is provided.

TABLE III

| Sample | Tube Design | Transition Location | Input Work (g-cm) |
|---|---|---|---|
| Sample A | Polyamide (proximal outer) Pebax blend (distal outer) MA/PE (middle) PE (inside) | 7 cm | 271 |
| Sample B | Polyamide (proximal outer) Pebax blend (distal outer) MA/PE (middle) PE (inside) | 2.5 cm | 291.4 |
| Sample C | Polyamide (proximal outer) Pebax blend (distal outer) MA/PE (middle) PE (inside) | 1 cm | 298.6 |

The inner tube has proximal and distal sections composed as described above in Bi-Component Sample 1 of Table II. Sample A has a transition location 7 cm from the distal end, Sample B has a 2.5 cm transition location and Sample C has a 1 cm transition location. As the data indicates, Sample A, having a 7 cm transition location, required substantially less input work to traverse the test path compared to bi-component samples having 1 cm and 2.5 cm transition locations.

Figure 9:
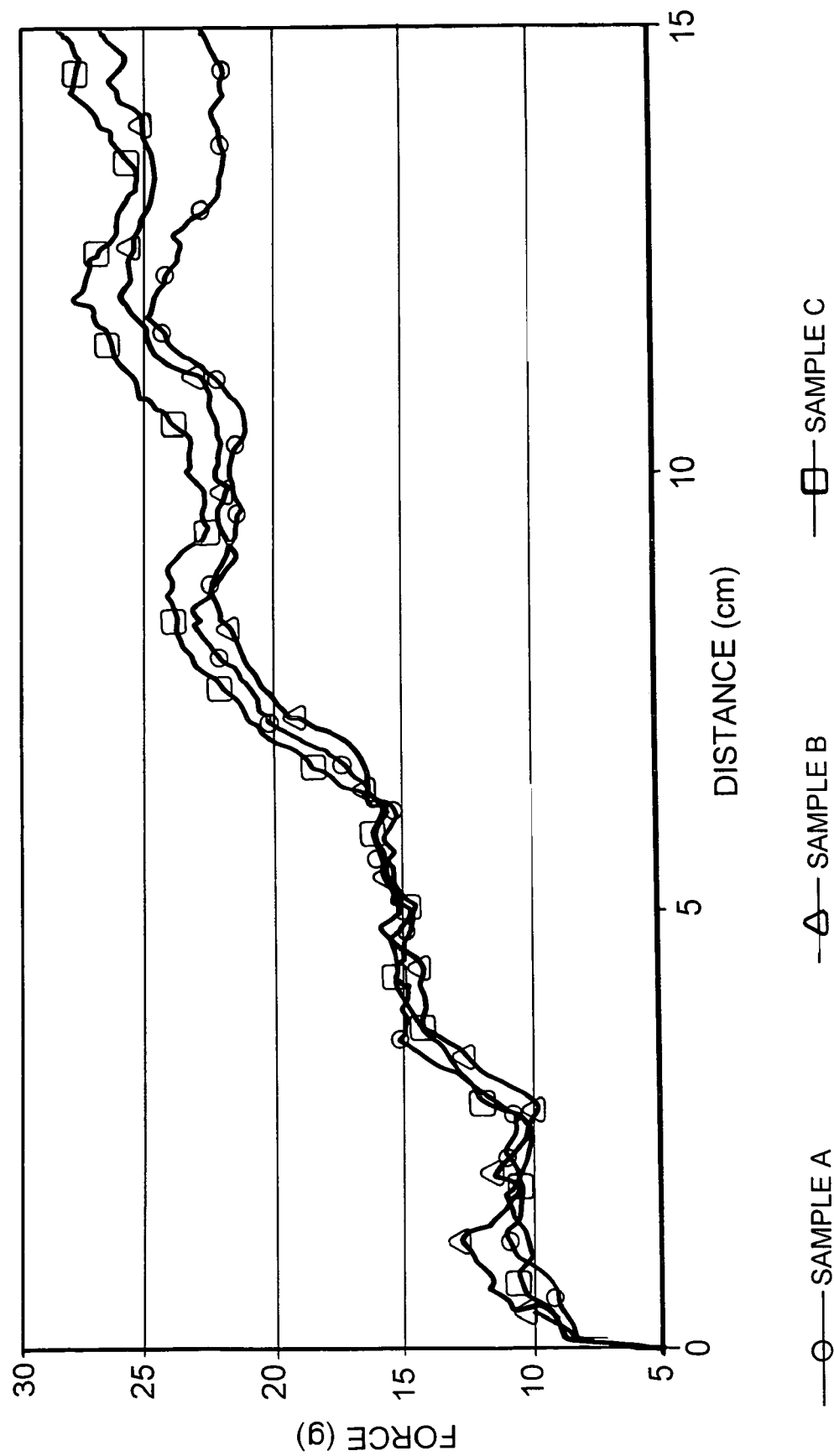
FIG. 9 is a plot of force as a function of distance along a track.

Referring as well to FIG. 9, a plot of input force as a function of the path distance for catheter assemblies in Table III is provided. As the graph indicates, Sample A provides substantially improved trackability at longer path distances.

Other Embodiments

Referring to FIG. 10, a catheter 150 having a body 152 defining side by side lumens is illustrated. A first lumen 154 extends substantially the length of the catheter for use in guide wire delivery. A second lumen 156 provides inflation fluid to the balloon. The body 152 has a proximal portion 158, a distal portion 160 and a transition 162 at a position P from the distal end of the tube. The proximal and distal portions can be formed of different materials and/or different cross-sectional dimensions to vary the flexibility of the portions about the transition as discussed above. The proximal and distal portions can include multiple polymer layers as described above.

Referring to FIG. 11, in another embodiment, a catheter body 172 having more than two sections, in this case sections 174, 176, 178. A transition 180 between first sections 174 and 176 is provided at a position, P, from the distal end of the catheter. The first section 176 may have a relatively high flexural modulus and the second section may have a relatively low flexural modulus. The section 178 may include a radiopaque material such as a metal to facilitate monitoring the catheter by fluoroscopy. The section 178 may also be made of a very soft polymer with a relatively small diameter to provide an atraumetic distal tip. The section 178 can be positioned distal of the balloon. In other embodiments, the proximal section 174 can be composed of multiple subsections of different column strengths, composition and/or diameter.

In further embodiments, the catheter body is a rapid-exchange type catheter body which includes a pathway for the guide wire to exit at a location distal to the proximal end and proximal of the balloon. In further embodiments, the balloon catheter can be arranged for use in non-vascular applications such as the esophagus, the gastrointestinal tract, or the urinary tract.

What is claimed is:

1. A concentric balloon catheter, comprising:
   a polymeric outer tubular member defining a lumen, and
   a polymeric inner tubular member, the polymeric inner tubular member located within the lumen of the outer tubular member and a balloon spanning the inner and the outer tubular members, the inner tubular member comprising multiple layers, the inner tubular member having a first, proximal section welded to a second more distal section to define a transition, and comprising three or more layers in each of the first and second sections, the second section having a column strength of about 75 percent or less than the column strength of the first section per 2.54 centimeters, the transition located about one to ten centimeters from the distal end of the inner tubular member.

2. The catheter of claim 1 wherein the transition is about four to about seven centimeters from the distal end of the inner tubular member.

3. The catheter of claim 1 wherein the first section has a column strength, per 2.54 centimeters, of about five grams to 20 grams and the second section has a column strength, per 2.54 centimeters, of about two grams to seven grams.

4. The catheter of claim 1 wherein the transition is located proximal of the balloon.

5. The catheter of claim 1 wherein the inner tubular member has a push strength of about 15 g/cm or more.

6. The catheter of claim 1 wherein the first and second sections have different diameters.

7. The catheter of claim 6 wherein the first and second sections have the same polymer composition.

8. The catheter of claim 1 wherein the first and second sections have different polymer compositions.

9. The catheter of claim 1 wherein the first section includes an innermost layer and the second section includes the same innermost layer as the first section.

10. The catheter of claim 1 wherein a second layer in both the proximal and distal sections is elastomeric.

11. The catheter of claim 10 wherein the second layers in the proximal and distal sections have different durometers.

12. The catheter of claim 11 including a bonding layer between the innermost and second layers.

13. The catheter of claim 1 comprising a vascular angioplasty catheter.

14. The catheter of claim 1 wherein the balloon is formed of a semi-compliant material.

15. The catheter of claim 1 wherein a stent is disposed over the balloon.

16. The catheter of claim 1 wherein the transition is located about two to nine centimeters from the distal end of the inner tubular member.

17. The catheter of claim 1 wherein the transition is located about four to eight centimeters from the distal end of the inner tubular member.

18. The catheter of claim 1 wherein the transition is located about four to about 7.5 centimeters from the distal end of the inner tubular member.

19. The catheter of claim 1, wherein the first proximal section and the second more distal section each include an outer layer, the outer layer of the first proximal section comprising a first polymeric material and the outer layer of the second more distal section comprising a second polymeric material that is different from the first polymeric material.

20. The catheter of claim 1, wherein the first and second sections comprise separate tubular elements, ends of the first and second sections being welded together.

21. The catheter of claim 1, wherein the transition is located proximal to a distal end of the balloon.

* * * * *